United States Patent
van Zee

(10) Patent No.: US 10,939,635 B2
(45) Date of Patent: Mar. 9, 2021

(54) LETTUCE VARIETY NUN 07839 LTL

(71) Applicant: NUNHEMS B.V., Nunhem (NL)

(72) Inventor: Johan Engelbert van Zee, Zaltbommel (NL)

(73) Assignee: NUNHEMS B.V., Nunhem (NL)

( * ) Notice: Subject to any disclaimer, the term of this patent is extended or adjusted under 35 U.S.C. 154(b) by 42 days.

(21) Appl. No.: 16/422,111

(22) Filed: May 24, 2019

(65) Prior Publication Data

US 2019/0274271 A1    Sep. 12, 2019

Related U.S. Application Data

(63) Continuation-in-part of application No. 15/903,573, filed on Feb. 23, 2018, now abandoned.

(60) Provisional application No. 62/555,079, filed on Sep. 7, 2017.

(51) Int. Cl.
*A01H 6/14* (2018.01)
*A01H 5/12* (2018.01)

(52) U.S. Cl.
CPC .............. *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 7,579,519 B1 | 8/2009 | Knerr | |
| 8,785,729 B2 * | 7/2014 | van Schijndel | A01H 5/12 800/305 |
| 2008/0222949 A1 | 9/2008 | Bissonnette et al. | |
| 2015/0126380 A1 | 5/2015 | Van Dun | |

FOREIGN PATENT DOCUMENTS

EP         1197137 A1    4/2002

OTHER PUBLICATIONS

USDA Department of Agriculture, Agricultural Marketing Service, "Objective Description of Variety—Lettuce (*Lactuca sativa* L.)" ams.usda.gov/ under sites/default/files/media/01-Lettuce%20ST-470-01%202015.pdf, Jun. 2015.

UPOV, "Guidelines for the Conduct of Tests for Distinctness, Uniformity and Stability", TG'/013/11 (Geneva 2006, last updated 2017) http://www.upov.int/edocs/tgdocs/en/tg013.pdf, Apr. 5, 2017.
Allard, Robert W., "Principles of Plant Breeding", Second Edition, John Wiley & Sons, Inc., pp. 119-128, 1960.
Brotman, Y. et al., "Resistance Gene Homologues in Melon are Linked to Genetic Loci Conferring Disease and Pest Resistance", Theor Appl Genet, vol. 104, pp. 1055-1063, Published online Feb. 8, 2002.
Clewer, A. et al., "Practical Statistics and Experimental Design for Plant and Crop Science", John Wiley & Sons, Ltd, 2001.
Dziechciarková, M. et al, "Characterization of Lactuca sapp. Germplasm by Protein and Molecular Markers—a review," Plant Soil Environ., vol. 50, pp. 47-58, 2004.
Gonai, T. et al., "Abscisic Acid in the Thermoinhibition of Lettuce Seed Germination and Enhancement of its Catabolism by Gibberellin", Journal of Experimental Botany, vol. 55, No. 394, pp. 111-118, Jan. 2004.
Turini, T. et al., "Iceberg Lettuce Production in California," University of California Agriculture and Natural Resources, Publication 7215, 2011.
Smith, R. et al., "Leaf Lettuce Production in California," University of California Agriculture and Natural Resources, Publication 7216, 2011.
Needleman, S. et al., "A General Method Applicable to the Search for Similarities in the Amino Acid Sequence of Two Proteins," Journal of Molecular Biology, vol. 48, pp. 443-453, 1970.
Parvathaneni, R. et al., "Fingerprinting in Cucumber and Melon (*Cucumis* spp.) Genotypes Using Morphological and ISSR Markers," J. Crop Sci. Biotech., vol. 14, No. 1, pp. 39-43, Mar. 2011.
Rice, P. et al., "EMBOSS: The European Molecular Biology Open Software Suite," Trends in Genetics, vol. 16, Issue 6, pp. 276-277, Jun. 2000.
Teng, W. et al., "Rapid Regeneration of Lettuce from Suspension Culture," HortScience, vol. 27, No. 9, pp. 1030-1032, 1992.
Teng, W. et al., "Regenerating Lettuce from Suspension Culture in a 2-Liter Bioreactor", HortScience, vol. 28, No. 6, pp. 669-671, 1993.
Vidavsky, F. et al., "Tomato Breeding Lines Resistant and Tolerant to Tomato Yellow Leaf Curl Virus Issued from *Lycopersicon hirsutum*", Phytopathology, vol. 88, No. 9, pp. 910-914, 1998.
Vos, P. et al., "AFLP: A New Technique for DNA Fingerprinting," Nucleic Acids Research, vol. 23, No. 21, pp. 4407-4414, 1995.
Zhang X. et al., "Genotypic Effects on Tissue Culture Response of Lettuce Cotyledons," Journal of Genetics and Breeding vol. 46, No. 3, pp. 287-290, 1992.

\* cited by examiner

*Primary Examiner* — Ashley K Buran

(74) *Attorney, Agent, or Firm* — Arent Fox LLP

(57) ABSTRACT

A new and distinct variety of lettuce variety NUN 07839 LTL is disclosed as well as seeds and plants and heads or leaves thereof. NUN 07839 LTL is a red oak baby leaf lettuce variety, comprising resistance to Downy Mildew (*Bremia lactutae*) isolates Bl:16-35 EU and *Nasonovia ribisnigri* biotype Nr:0.

20 Claims, No Drawings

LETTUCE VARIETY NUN 07839 LTL

CROSS-REFERENCE TO RELATED APPLICATION

This application is a continuation-in-part of U.S. patent application Ser. No. 15/903,573, filed on Feb. 23, 2018, which claims priority to U.S. Provisional Patent Application No. 62/555,079 filed on Sep. 7, 2017, which are hereby incorporated by reference in their entireties.

FIELD OF THE DISCLOSURE

The disclosure relates to the field of plant breeding and, more specifically, to the development of lettuce variety NUN 07839 LTL (also designated as NUN 07839 or 07839 LTL or NUN 07839 or 07839 LTL. The disclosure further relates to vegetative reproductions of lettuce variety NUN 07839 LTL, methods for tissue culture of lettuce variety NUN 07839 LTL, and to phenotypic variants of lettuce variety NUN 07839 LTL.

BACKGROUND OF THE DISCLOSURE

The goal of vegetable breeding is to combine various desirable traits in a single variety. Such desirable traits may include greater yield, resistance to diseases, insects or other pests, tolerance to heat and drought, better agronomic quality, higher nutritional value, enhanced growth rate, and improved shelf life.

The development of commercial lettuce cultivars or varieties requires the crossing of lettuce plants, and the evaluation of the crosses. Pedigree breeding and recurrent selection are examples of breeding methods used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

All cultivated forms of lettuce belong to the highly polymorphic species *Lactuca sativa* that is grown for its edible head and leaves. *Lactuca sativa* is in the Asteraceae (Compositae) family. Lettuce is related to chicory, sunflower, aster, dandelion, artichoke, and chrysanthemum. *L. sativa* is one of about 300 species in the genus *Lactuca*. There are many types of lettuce, and new types are constantly in development. Types of lettuce include Cutting/Leaf, Iceberg/Crisphead, Cos or Romaine, Batavian, Salinas Group, Latin, Butterhead, Great Lakes Group, Eastern (Ithaca) Group, Bibb, Vanguard Group, Multileaf, or Stem lettuce. Lettuce is typically consumed fresh and occasionally as a cooked vegetable. It is popularly used in salads, wraps, and sandwiches.

Fresh lettuce is available in the United States year-round although the greatest supply is from May through October. For planting purposes, the lettuce season is typically divided into three categories, early, mid and late, with the coastal areas planting from January to August, and the desert regions planting from August to December. California and Arizona are the two largest producers of lettuce in the United States.

Changes in lifestyle primarily due to increasing health awareness results to growing demand for healthy convenience food. Supermarkets, restaurants, catering firms, and convenience stores are constantly looking for more colorful garnishing for sandwiches, wraps, and ready-to-eat snacks such as salads. The changing food and consumer trends present opportunities for breeding companies to develop new varieties with specific shapes of leaves, specific average size of leaves, prominent color, glossiness, taste, and a wide variety of texture. Other breeding objectives include disease or pest resistance, yield, prolonged shelf life, and suitability to climatic requirements.

SUMMARY OF VARIOUS ASPECTS OF THE DISCLOSURE

The disclosure provides for a lettuce variety NUN 07839 LTL, products thereof, and methods of using the same. NUN 07839 LTL is a red oak baby leaf lettuce variety and is suitable for growing in the open field.

In one aspect, the disclosure provides a seed of lettuce variety NUN 07839 LTL, wherein a representative sample of said seed has been deposited under Accession Number NCIMB 42969. The disclosure also provides for a plurality of seeds of lettuce variety NUN 07839 LTL. The lettuce seed of variety NUN 07839 LTL may be provided as an essentially homogeneous population of lettuce seed. The population of seed of lettuce variety NUN 07839 LTL may be particularly defined as an essentially free from other seed. The seed population may be grown into plants to provide an essentially homogeneous population of lettuce plants described herein.

The disclosure also provides a plant grown from a seed of lettuce variety NUN 07839 LTL and a plant part thereof. In another aspect, the disclosure provides for an inbred variety of NUN 07839 LTL. The disclosure also provides for a progeny of lettuce variety NUN 07839 LTL. In another aspect, the disclosure provides a plant or a progeny retaining all or all but one, two, or three of the "distinguishing characteristics" of lettuce variety NUN 07839 LTL, and methods of producing that plant or progeny.

In another aspect, the disclosure provides a plant or a progeny having all of the physiological and morphological characteristics of lettuce variety NUN 07839 LTL, when grown under the same environmental conditions. In another aspect, the plant or progeny has all or all but one, two, or three of the physiological and morphological characteristics of lettuce variety NUN 07839 LTL when grown under the same environmental conditions and e.g., evaluated at significance levels of 1%, 5%, or 10% significance (which can be expressed as a p-value) for quantitative characteristics, wherein a representative sample of seed of variety NUN 07839 LTL has been deposited under Accession Number NCIMB 42969. In another aspect, the plant or progeny has all or all but one, two, or three of the physiological and morphological characteristics as listed in Tables 1 and 2 of lettuce variety NUN 07839 LTL when measured under the same environmental conditions and e.g., evaluated at significance levels of 1%, 5%, or 10% significance (which can also be expressed as a p value) for quantitative characteristics.

In another aspect a plant of lettuce variety NUN 07839 LTL or a progeny thereof has plants has 17, 18, or more or all of the following distinguishing characteristics when compared to Reference Variety NUN 9044 LT (Redglace) as shown in Table 3: 1) longer fourth leaf length; 2) narrower fourth leaf width; 3) longer mature leaf length; 4) wider mature leaf width; 5) taller plant height; 6) wider plant spread; 7) heavier plant weight; 8) longer core height; 9) larger core diameter; 10) entire fourth leaf apical margin; 11) coarsely dentate fourth leaf basal margin; 12) slight undulation of fourth leaf margin; 13) deep incision of mature leaf margin; 14) medium density incision of mature leaf margin; 15) shallowly dentate indentation of mature leaf margin; 16) moderate undulation of mature leaf apical margin; 17) moderate mature leaf blistering; and 18) greyed-purple mature leaf color.

In another aspect, a plant of lettuce variety NUN 07839 LTL or a part thereof comprises resistance to Downy Mildew (*Bremia lactutae*) isolates Bl:16-35 EU and *Nasonovia ribisnigri* biotype Nr:0, measured according to UPOV standards described in TG/13/11.

In another aspect, the disclosure provides for a plant part obtained from lettuce variety NUN 07839 LTL, wherein said plant part is: a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a pistil, an anther, or a flower or a part thereof. Heads and leaves are particularly important plant parts. In another aspect, the plant part obtained from variety NUN 07839 LTL is a cell, optionally a cell in a cell or tissue culture. That cell may be grown into a plant of lettuce variety NUN 07839 LTL.

The disclosure also provides a cell culture of lettuce variety NUN 07839 LTL and a plant regenerated from lettuce variety NUN 07839 LTL, wherein the plant has all of the characteristics of lettuce variety NUN 07839 LTL when grown under the same environmental conditions, as well as methods for culturing and regenerating lettuce variety NUN 07839 LTL. Alternatively, a regenerated plant may have one characteristic that is different from lettuce variety NUN 07839 LTL.

The disclosure further provides a vegetatively propagated plant of variety NUN 07839 LTL having all or all but one, two, or three of the morphological and physiological characteristics of lettuce variety NUN 07839 LTL when grown under the same environmental conditions.

The disclosure also provides a lettuce head and/or a lettuce leaf produced on a plant grown from a seed of lettuce variety NUN 07839 LTL.

In another aspect, the disclosure provides a seed growing or grown on a plant of lettuce variety NUN 07839 LTL (e.g., produced after pollination of the flower of lettuce variety NUN 07839 LTL). The disclosure also provides for an F1 progeny of lettuce variety NUN 07839 LTL.

Definitions

"Lettuce" refers herein to plants of the species *Lactuca sativa* L. The most commonly eaten parts of a lettuce plant are the head or a leaf. The head comprises a core and leaves, which may be divided in inner and outer leaves.

"Cultivated lettuce" refers to plants of *Lactuca sativa* (e.g., varieties, breeding lines or cultivars of the species *L. sativa* as well as crossbreds thereof, or crossbreds with other *Lactuca sativa* species, or even with other *Lactuca* species), cultivated by humans and having good agronomic characteristics.

The terms "lettuce plant designated NUN 07839 LTL," "NUN 07839 LTL," "inbred NUN 7839," "07839 LTL," or "lettuce 7839" are used interchangeably herein and refer to a lettuce plant of variety NUN 07839 LTL, representative seed of has been deposited under Accession Number NCIMB 42969.

A "seed of lettuce variety NUN 07839 LTL" refers to a lettuce seed which can be grown into a plant of lettuce variety NUN 07839 LTL, wherein a representative sample of viable seeds of lettuce variety NUN 07839 LTL has been deposited under Accession Number NCIMB 42969. A seed can be in any stage of maturity, for example, a mature, viable seed, or an immature non-viable seed. A seed comprises an embryo and maternal tissues.

An "embryo of lettuce variety NUN 07839 LTL" refers to an embryo as present in a seed of lettuce variety NUN 07839 LTL, a representative sample of seed of NUN 07839 LTL having been deposited under Accession Number NCIMB 42969.

A "seed grown on lettuce variety NUN 07839 LTL" refers to a seed grown on a mature plant of variety NUN 07839 LTL or inside a fruit of lettuce variety NUN 07839 LTL. The "seed grown on lettuce variety NUN 07839 LTL" contains tissues and DNA of the maternal parent, lettuce variety NUN 07839 LTL. The "seed grown on lettuce variety NUN 07839 LTL" contains an F1 embryo. When said seed is planted, it grows into a first generation progeny plant of variety NUN 07839 LTL. Since NUN 07839 LTL is an inbred variety and thus highly homozygous, the set of chromosomes inherited by the first generation is predictable.

An "essentially homogeneous population of lettuce seed" is a population of seeds where at least 77%, 98%, 99% or more of the total population of seed are seed of lettuce variety NUN 07839 LTL.

An "essentially homogeneous population of lettuce plants" is a population of plants where at least 97%, 97%, 99% or more of the total population of plants are plants of lettuce variety NUN 07839 LTL.

The phrase "essentially free from other seed" refers to a population of seeds where less than 3%, 2%, 1%, or even less, of the total population of seed is seed that is not a lettuce seed or, in another option, less than 3%, 2%, 1%, or less, of the total population of seed is seed that is not seed of lettuce variety NUN 07839 LTL.

"USDA descriptors" are the plant variety descriptors described for lettuce in the "Objective description of Variety—Lettuce (*Lactuca sativa* L.)," as published by U.S. Department of Agriculture, Agricultural Marketing Service, Science and Technology, Plant Variety Protection Office, Beltsville, Md. 20705 and which can be downloaded from the world-wide web at ams.usda.gov/under services/plant-variety-protection/pvpo-c-forms under lettuce. "Non-USDA descriptors" are other descriptors suitable for describing lettuce.

"UPOV descriptors" are the plant variety descriptors described for lettuce in the "Guidelines for the Conduct of Tests for Distinctness, Uniformity and Stability," TG/13/11 (Geneva 2006, last updated 2017 Apr. 5), as published by UPOV (International Union for the Protection of New Varieties and Plants) and which can be downloaded from the world-wide web at upov.int/under edocs/tgdocs/en/tg013.pdf, which is hereby incorporated by reference in its entirety. Likewise, "UPOV methods" to determine specific parameters for the characterization of lettuce are described at upov.int.

"RHS" or "RHS color" refers to the color chart of the Royal Horticultural Society (UK), which publishes a botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart 2007.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, or a flower. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant (e.g., from lettuce variety NUN 07839 LTL). An F1 progeny produced from self-pollination of the inbred variety NUN 07839 LTL will thus comprise two sets of chromosomes derived from lettuce variety NUN 07839 LTL, while an F1 progeny derived from cross-fertilization of NUN 07839 LTL will comprise only one set of chromosomes from lettuce variety NUN 07839 LTL and the other set of chromosomes from the other parent.

"Reference Variety" refers herein to variety NUN 9044 LT, a variety from Nunhems B.V. with commercial name Redglace, which has been planted in a trial together with NUN 07839 LTL. The characteristics of lettuce variety NUN 07839 LTL were compared with the characteristics of the Reference Variety as shown in Tables 1 and 2. The distinguishing characteristics between lettuce variety NUN 07839 LTL and the Reference Variety are shown in Table 3.

"Head" as used herein refers to lettuce heads, i.e., the plant without the root system, for example, substantially all harvested leaves. Encompassed are immature leaves (e.g., "baby leaf") and mature leaves.

The "base" of a plant is the part of a lettuce plant where the leaves are attached to the root system of the plant.

"Core length" of the internal lettuce stem is measured from the base of the cut and trimmed head to the tip of the stem.

"Head weight" refers to the mean weight of saleable lettuce head, cut, and trimmed to market specifications.

"Head diameter" refers to the mean diameter of the cut and trimmed head, sliced vertically, and measured at the widest point perpendicular to the stem.

"Head height" refers to the mean height of the cut and trimmed head, sliced vertically, and measured from the base of the cut stem to the leaf tip.

"Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Harvested plant material" refers herein to plant parts (e.g., leaves or heads detached from the whole plant) which have been collected for further storage and/or further use.

"Harvested seeds" refers to seeds harvested from a line or variety, e.g., produced after self-fertilization or cross-fertilization and collected.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant."

"Marketable yield" means the total weight of all marketable lettuce heads or leaves harvested per hectare of a particular line or variety, e.g., lettuce heads or leaves suitable for being sold for fresh consumption, having good color, glossiness size and texture and no or very low levels of deficiencies. A "marketable lettuce head or leaf" is a head or leaf that has commercial value.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the progenitor parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1 and 2 or "all or all but one, two or three of the physiological and morphological characteristics" of Tables 1 and 2.

The physiological and/or morphological characteristics mentioned above are commonly evaluated at significance levels of 1%, 5%, or 10% if they are numerical (quantitative), or for having an identical degree (or type) if not numerical (not quantitative), if measured under the same environmental conditions. For example, a progeny plant or a single locus converted plant or a mutated plant of lettuce variety NUN 07839 LTL may have one or more (or all) of the essential physiological and/or morphological characteristics of said variety listed in Tables 1 and 2, as determined at the 5% significance level (i.e., $p<0.05$), when grown under the same environmental conditions.

"Distinguishing characteristics" or "distinguishing morphological and/or physiological characteristics" refers herein to the characteristics which distinguish a new variety from other lettuce varieties (i.e., are different), when grown under the same environmental conditions. The distinguishing characteristics between lettuce variety NUN 07839 LTL and the Reference Variety (NUN 9044 LT) are described Table 3. When comparing lettuce variety NUN 07839 LTL with different varieties, the distinguishing characteristics will be different. In one aspect, the distinguishing characteristics may therefore include at least one, two, three or more (or all) of the characteristics listed in Tables 1 and 2. All numerical distinguishing characteristics are statistically significantly different at $p<0.05$ between lettuce variety NUN 07839 LTL and the other variety (e.g., the Reference Variety).

Lettuce Variety NUN 07839 LTL has the following distinguishing characteristics when compared to the Reference Variety NUN 9044 LT as shown in Table 3: 1) longer fourth leaf length; 2) narrower fourth leaf width; 3) longer mature leaf length; 4) wider mature leaf width; 5) taller plant height; 6) wider plant spread; 7) heavier plant weight; 8) longer core height; 9) larger core diameter; 10) entire fourth leaf apical margin; 11) coarsely dentate fourth leaf basal margin; 12) slight undulation of fourth leaf margin; 13) deep incision of mature leaf margin; 14) medium density incision of mature leaf margin; 15) shallowly dentate indentation of mature leaf margin; 16) moderate undulation of mature leaf apical margin; 17) moderate mature leaf blistering; and 18) greyed-purple mature leaf color, when grown under the same environmental conditions.

Thus, a lettuce plant "comprising the distinguishing characteristics of lettuce variety NUN 07839 LTL" (such as a progeny plant) refers herein to a plant which does not differ from said variety in the distinguishing characteristics above. Therefore, in one aspect, the disclosure provides a plant that does not differ from lettuce variety NUN 07839 LTL in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using one way Analysis of variance (ANOVA), a standard method known to the skilled person. Non-numerical or "degree" or "type" characteristic is considered "the same" when the values have the same "degree" or "type" when scored using USDA and/or UPOV descriptors, if the plants are grown under the same environmental conditions.

"Plant line" is, for example, an inbred variety or a breeding line which can be used to develop one or more varieties. Both are typically highly homozygous. Progeny obtained by selfing such a plant line has the same phenotype as its parents.

"Inbred variety" refers to an inbred (nearly homozygous) line or seeds thereof. For example, the (nearly homozygous) plant is self-pollinated or the (nearly homozygous) female parent is pollinated with pollen of the same plant line to produce inbred seeds on the female parent.

"Tissue Culture" refers to a composition comprising isolated cells of the same or a different type or a collection of such cells organized into parts of a plant. Tissue culture of various tissues of lettuce and regeneration of plants therefrom is well known and widely published (see, e.g., Teng et al., HortScience. 1992, 27(9): 1030-1032; Teng et al., HortScience. 1993, 28(6): 669-1671; Zhang et al., Journal of Genetics and Breeding. 1992, 46(3): 287-290). Similarly, methods of preparing cell cultures are known in the art.

"Vegetative propagation," "vegetative reproduction," or "clonal propagation" are used interchangeably herein and mean the method of taking part of a plant and allowing that plant part to form at least roots, and also refer to the plant or plantlet obtained by that method. Optionally, the vegetative propagation is grown into a mature plant.

"Regeneration" refers to the development of a plant from cell culture or tissue culture or vegetative propagation.

"Crossing" refers to the mating of two parent plants. The term encompasses "cross-pollination" and "selfing."

"Selfing" refers to self-pollination of a plant, i.e., the transfer of pollen from the anther to the stigma of the same plant.

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (e.g., methods other than genetic modification/transformation/transgenic methods), by which, for example, a genetically heritable trait can be transferred from one lettuce line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant." The technique can also be used on a parental line of a hybrid.

"Progeny" as used herein refers to a plant obtained from a plant designated NUN 07839 LTL. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another lettuce plant of the same or another variety or line, or wild lettuce plants. A progeny may comprise a mutation or a transgene. A "first generation progeny" is the progeny is directly derived from, obtained from, obtainable from or derivable from the parent plant by, e.g., traditional breeding methods (selfing and/or cross-pollinating) or regeneration (optionally combined with transformation or mutation). Thus, a plant of lettuce variety NUN 07839 LTL is the male parent, the female parent, or both of a first generation progeny of lettuce variety NUN 07839 LTL. Progeny may have all of the physiological and morphological characteristics of lettuce variety NUN 07839 LTL when grown under the same environmental conditions. Using methods such as backcrossing, recurrent selection, mutation or transformation, one or more specific characteristics may be introduced into said variety, or to a plant comprising all but one, two, or three of the morphological and physiological characteristics of lettuce variety NUN 07839 LTL.

The terms "gene converted," "conversion plant," or "single locus converted plant" in this context refer to lettuce plants which are developed by traditional backcrossing techniques, e.g., backcrossing, or via genetic engineering or through mutation breeding, wherein essentially all of the desired morphological and physiological characteristics of parent variety or line are recovered, in addition to the one or more characteristics introduced into the parent via e.g., backcrossing technique (optionally including reverse synthesis of breeding line). It is understood that only the addition of a further characteristic (e.g., addition of gene conferring a further characteristic, such as a disease resistance gene), but also the replacement/modification of an existing characteristic by a different characteristic is encompassed herein (e.g., a mutant allele of a gene can modify the phenotype of a characteristic).

Likewise, a "Single Locus Converted (Conversion) Plant" refers to plants developed by plant breeding techniques comprising or consisting of mutation breeding and/or by genetic transformation and/or by traditional breeding techniques, such as backcrossing, wherein essentially all of the desired morphological and physiological characteristics of a lettuce variety are recovered in addition to the characteristics of the single locus having been transferred into the variety via the above-mentioned techniques, or wherein a morphological and physiological characteristic of the variety has been replaced/modified in the variety. In case of a hybrid, the gene may be introduced, or modified, in the male or female parental line.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for lettuce variety NUN 07839 LTL. The mean, if not indicated otherwise within this application, refers to the arithmetic mean of measurements on at least 10 different, randomly selected plants of a variety or line.

DETAILED DESCRIPTION OF VARIOUS ASPECTS OF THE DISCLOSURE

The disclosure relates to a plant of lettuce variety NUN 07839 LTL, wherein a representative sample of seeds of said variety has been deposited under Budapest Treaty, with Accession Number NCIMB 42969. NUN 07839 LTL is a red oak baby leaf lettuce variety and is suitable in growing in the open field.

The disclosure relates to a seed of lettuce variety NUN 07839 LTL, wherein a representative sample of said seed has been deposited under the Budapest Treaty with Accession Number NCIMB 42969.

In another aspect, the disclosure provides for a plant part of lettuce variety NUN 07839 LTL, preferably a head or a leaf, a representative sample of seed from said variety has been deposited under Accession Number NCIMB 42969.

A seed of inbred variety NUN 07839 LTL is obtainable by selfing the variety and harvesting the seeds produced. The resultant seeds can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coating or crop protection compounds. The seed produces a plant of lettuce variety NUN 07839 LTL.

Also provided is a plant of lettuce variety NUN 07839 LTL, or a head or a leaf or other plant part thereof, produced from a seed, wherein a representative sample of said seeds will be deposited under the Budapest Treaty, with Accession Number NCIMB 42969.

Also provided is a plant part obtained from variety NUN 07839 LTL, wherein said plant part is a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seed coat, or another maternal tissue which is part of a seed grown on a said variety, a hypocotyl, a cotyledon, a pistil, an anther, or a flower or a part thereof. Heads and leaves are particularly important plant parts. In a further aspect, the plant part obtained from variety NUN 07839 LTL is a cell, optionally a cell in a cell or tissue culture. The cell may be grown into a plant of lettuce variety NUN 07839 LTL. A part of lettuce variety NUN 07839 LTL (or of a progeny of that variety or of a plant having all of the physiological and morphological characteristics but one, two, or three of lettuce variety NUN 07839 LTL) further encompasses any cells, tissues, organs obtainable from the seedlings or plants in any stage of maturity.

The disclosure also provides for a food or feed product or a processed product comprising or consisting of a plant part described herein. Preferably, the plant part is a lettuce head or leaf or a part thereof and/or an extract from a leaf or another plant part described herein comprising at least one cell of lettuce variety NUN 07839 LTL. The food or feed product may be fresh or processed, e.g., dried, grinded, powdered, pickled, chopped, cooked, roasted, in a sauce, in a sandwich, pasted, pureed or concentrated, juiced, pickled, canned, steamed, boiled, fried, blanched and/or frozen, etc.

Such a plant part of lettuce variety NUN 07839 LTL can be stored and/or processed further. The disclosure thus also provides for a food or feed products comprising one or more of such parts, such as canned, chopped, cooked, roasted, in a sauce, in a sandwich, pasted, pureed or concentrated, juiced, frozen, dried, pickled, or powdered lettuce heads or leaves from variety NUN 07839 LTL or from progeny of said variety, or from a derived variety, such as a plant having all or all but one, two, or three of the physiological and/or morphological characteristics of lettuce variety NUN 07839 LTL.

In another aspect, the disclosure provides for a lettuce head or leaf of variety NUN 07839 LTL, or a part of a head or leaf of said variety. The head or leaf can be in any stage of maturity, for example, immature or mature. In another aspect, the disclosure provides for a container comprising or consisting of a plurality of harvested lettuce heads or leaves or parts of lettuce heads or leaves of said variety, or lettuce heads or leaves of progeny thereof, or lettuce heads or leaves of a derived variety. Marketable lettuce heads or leaves are generally sorted by size and quality after harvest. Alternatively, the lettuce heads or leaves can be sorted by leaf size, shape, texture, glossiness, or color.

In another aspect, the plant, plant part, or seed of lettuce variety NUN 07839 LTL is inside or more containers. For example, the disclosure provides containers such as cans, boxes, crates, bags, cartons, Modified Atmosphere Packaging Films (e.g., biodegradable films), etc. comprising a plant or part of a plant (fresh and/or processed) or seed of lettuce variety NUN 07839 LTL. In a particular aspect, the container comprises a plurality of seeds of lettuce variety NUN 07839 LTL, or a plurality of plant parts of lettuce variety NUN 07839 LTL.

The disclosure further relates to a lettuce variety NUN 07839 LTL, which when compared to Reference Variety NUN 9044 LT has the following distinguishing characteristics as shown in Table 3: 1) longer fourth leaf length; 2) narrower fourth leaf width; 3) longer mature leaf length; 4) wider mature leaf width; 5) taller plant height; 6) wider plant spread; 7) heavier plant weight; 8) longer core height; 9) larger core diameter; 10) entire fourth leaf apical margin; 11) coarsely dentate fourth leaf basal margin; 12) slight undulation of fourth leaf margin; 13) deep incision of mature leaf margin; 14) medium density incision of mature leaf margin; 15) shallowly dentate indentation of mature leaf margin; 16) moderate undulation of mature leaf apical margin; 17) moderate mature leaf blistering; and 18) greyed-purple mature leaf color, when the characteristics are determined at the 5% significance level for plants grown under the same environmental conditions. Also encompassed are parts of that plant.

In one aspect, a plant of lettuce variety NUN 07839 LTL or a progeny plant thereof comprises all of the morphological and/or physiological characteristics (i.e., average values, as indicated on the USDA Objective Description of variety—lettuce (unless indicated otherwise)) as shown in Tables 1 and 2, when the characteristics are determined at the 5% significance level for plants grown under the same environmental conditions. A part of this plant is also provided.

The disclosure further provides a lettuce plant which does not differ from the physiological and morphological characteristics of the plant of lettuce variety NUN 07839 LTL, as determined at the 1%, 2%, 3%, 4%, or 5% significance level, when grown under the same environmental conditions. In a particular aspect, the plants are measured in the same trial (e.g., the trial is conducted as recommended by the USDA or UPOV). The disclosure also comprises part of said plant, preferably a leaf or a part thereof.

In another aspect, a plant of lettuce variety NUN 07839 LTL or a part thereof comprises resistance to Downy Mildew (*Bremia lactutae*) isolates Bl:16-35 EU and *Nasonovia ribisnigri* biotype Nr:0, measured according to UPOV standards described in TG/13/11.

The disclosure also provides a tissue or cell culture comprising cells of lettuce variety NUN 07839 LTL. Such tissue culture can, for example, be grown on plates or in liquid culture or be frozen for long term storage. The cells of lettuce variety NUN 07839 LTL used to start the culture can be any plant part suitable for vegetative reproduction, or, in a particular aspect, can be one or more of: an embryo, a meristem, a cotyledon, a hypocotyl, pollen, a leaf, an anther, a root, a root tip, a petiole, a flower, a fruit, a seed, or a stem. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a lettuce plant regenerated from the tissue or cell culture of lettuce variety NUN 07839 LTL, wherein the regenerated plant is not different from lettuce variety NUN 07839 LTL in all, or all but one, two or three, of the physiological and morphological characteristics (determined at the 5% significance level when grown under the same conditions. Optionally, the plant has one, two, or three physiological or morphological characteristic that is different from lettuce variety NUN 07839 LTL, wherein the difference or modification is effected by mutation or transformation.

In another aspect, the disclosure provides a lettuce plant regenerated from the tissue or cell culture of variety NUN 07839 LTL, wherein the plant has all or all but one, two or three of the physiological and morphological characteristics of said variety determined at the 5% significance level when grown under the same environmental conditions. Similarity or difference of a characteristic is determined by measuring the characteristics of a representative number of plants grown under the same environmental conditions, determining whether type/degree characteristics are the same and determining whether numerical characteristics are different the 5% significance level.

Lettuce variety NUN 07839 LTL, or its progeny, or a plant having all physiological and/or morphological characteristics or all but one, two, or three which are different from those of lettuce variety NUN 07839 LTL, can also be reproduced using vegetative reproduction methods. Therefore, the disclosure provides for a method of producing a plant or plant part of lettuce variety NUN 07839 LTL, comprising vegetative reproduction of lettuce variety NUN 07839 LTL. Vegetative propagation comprises regenerating a whole plant from a plant part of lettuce variety NUN 07839 LTL or from a progeny or from a plant having all of the physiological and morphological characteristics of said variety or all but one, two, or three different characteristics, such as a cutting, a cell culture, or a tissue culture.

The disclosure also provides methods of vegetatively propagating a part of the plant of variety NUN 07839 LTL. In certain aspects, the method comprises: (a) cultivating tissue or cells capable of being propagated from lettuce variety NUN 07839 LTL to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plant. In one aspect, the method further comprises (c) growing plants from said rooted plantlets. Therefore, the method also comprises regenerating a whole plant from a part of lettuce variety NUN 07839 LTL. In a particular aspect, the part to be propagated is a cutting, a cell culture, or a tissue culture.

The disclosure also provides for a vegetatively propagated plant of variety NUN 07839 LTL (or from progeny of lettuce variety NUN 07839 LTL or from a plant having all but one, two, or three of the physiological and/or morphological characteristics of lettuce variety NUN 07839 LTL), wherein the plant has all of the physiological and morphological characteristics of lettuce variety NUN 07839 LTL when the characteristics are determined at the 5% significance level for plants grown under the same environmental conditions. In another aspect, the propagated plant has all but one, two, or three of the physiological and morphological characteristics of lettuce variety NUN 07839 LTL when the characteristics are determined at the 5% significance level for plants grown under the same environmental conditions. A part of said propagated plant or said propagated plant with one, two, or three differences is also provided.

In another aspect, the disclosure provides a method for producing a plant part, preferably a head or a leaf, comprising growing a plant of lettuce variety NUN 07839 LTL until it develops at least one leaf or develops a head, and optionally collecting the head or leaf. Preferably, the head or leaf is collected at harvest maturity. In another aspect, the leaf is collected at baby leaf stage. A plant of lettuce variety NUN 07839 LTL can be produced by seeding directly in the soil (e.g., field) or by germinating the seeds in controlled environment conditions (e.g., greenhouses, hydroponic cultures, etc.) and optionally transplanting the seedlings into the field (see, e.g., Gonai et al., J. of Exp. Bot., 55(394): 111, 2004; http://anrcatalog.ucanr.edu/pdf/7215.pdf; http://anrcatalog.ucanr.edu/pdf/7216.pdf). Lettuce may also be grown in tunnels. Moreover, said variety can be grown in hydroponic cultures as described in, e.g., US 2008/0222949, which is herein incorporated by reference in its entirety, and the skilled person is familiar with various types of hydroponic cultures. Alternatively, seed of lettuce variety NUN 07839 LTL may be grown on peat block for use as root ball lettuce. Furthermore, said variety may be combined with 1, 2 or 3 different lettuce varieties to be grown as "composite lettuce" (see, e.g., EP 1 197 137, which is herein incorporated by reference in its entirety).

In still another aspect, the disclosure provides a method of producing a lettuce plant, comprising crossing a plant of lettuce variety NUN 07839 LTL with a second lettuce plant at least once, allowing the seed to develop and optionally harvesting said progeny seed. The skilled person can select a progeny lettuce plant from said crossing. Optionally, the progeny (grown from the progeny seed) is crossed twice, thrice, or four, six or seven times, and allowed to set seed. In one aspect, the first "crossing" further comprises planting seeds of a first and a second parent lettuce plant, often in proximity so that pollination will occur; for example, mediated by insect vectors. Alternatively, pollen can be transferred manually. Where the plant is self-pollinated, pollination may occur without the need for direct human intervention other than plant cultivation. After pollination, the plant can produce seed.

In yet another aspect, the disclosure provides a method of producing a plant, comprising selfing a plant of variety NUN 07839 LTL one or more times, and selecting a progeny plant from said selfing. In one aspect, the progeny plant retains all or all but one, two, or three of the physiological and morphological characteristics of lettuce variety NUN 07839 LTL when grown under the same environmental conditions. In a different aspect, the progeny plant comprises all (or all but one, two or three) of the physiological and morphological characteristic of lettuce variety NUN 07839 LTL of Tables 1 and 2.

In other aspects, the disclosure provides for a progeny plant of variety NUN 07839 LTL such as a progeny plant obtained by further breeding of lettuce variety NUN 07839 LTL. Further breeding with said variety includes selfing and/or cross-pollinating lettuce variety NUN 07839 LTL with another lettuce plant or variety one or more times. In particular, the disclosure provides for a progeny plant that retains all the morphological and physiological characteristics of lettuce variety NUN 07839 LTL or, in another aspect, progeny that retain all or all but one, two or three of the morphological and physiological characteristics of lettuce variety NUN 07839 LTL, optionally all or all but one, two or three of the morphological and physiological characteristics listed in Tables 1 and 2, determined at the 5% significance level for numerical characteristics, when grown under the same environmental conditions. In another aspect, the disclosure provides for a vegetative reproduction of the variety and a plant having all or all but 1, 2, or 3 of the physiological and morphological characteristics of lettuce variety NUN 07839 LTL (e.g., as listed in Tables 1 and 2).

The disclosure also provides a method for collecting pollen of lettuce variety NUN 07839 LTL, comprising collecting pollen from a plant of variety NUN 07839 LTL. Alternatively, the method comprises growing a plant of lettuce variety NUN 07839 LTL until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a lettuce flower.

The morphological and/or physiological differences between two different individual plants described herein (e.g., between lettuce variety NUN 07839 LTL and a progeny of lettuce variety NUN 07839 LTL) or between a plant of lettuce variety NUN 07839 LTL or progeny of said variety, or a plant having all, or all but 1, 2, or 3 of the physiological and morphological characteristics of lettuce variety NUN 07839 LTL (or all, or all but 1, 2, or 3 of the characteristics as listed in Tables 1 and 2) and another known variety can easily be established by growing said variety next to the each other or next to the other variety (e.g., in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, maturity, leaf shape, size and texture, leaf color and glossiness, bolt shape, surface and length, flower size and color, head weight, disease resistance, insect resistance, and resistance to physiological stress can be measured and directly compared for species of lettuce. Thus, the disclosure comprises a lettuce plant having one, two, or three of the physiological and/or morphological characteristics which are different from those of the plant of lettuce variety NUN 07839 LTL, and which otherwise has all of the physiological and morphological characteristics of the plant of lettuce variety NUN 07839 LTL, when determined at the 5% significance level for plants grown under the same environmental conditions. In one aspect, the different characteristic(s) is/are a result of breeding with lettuce variety NUN 07839 LTL and selection of a progeny plant comprising one, two, or three characteristics which are different than in lettuce variety NUN 07839 LTL. In another aspect, the different characteristic is the result of a mutation (e.g., spontaneous mutation or a human induced mutation through e.g., targeted mutagenesis or traditional mutagenesis such as chemically or radiation induced mutagenesis), or it is the result of transformation.

The morphological and physiological characteristics (and the distinguishing characteristics) of lettuce variety NUN 07839 LTL are provided, for example, in Tables 1 and 2. Encompassed herein is also a plant obtainable from lettuce variety NUN 07839 LTL (e.g., by selfing and/or crossing and/or backcrossing with said variety and/or progeny of said variety) comprising all or all but one, two or three of the physiological and morphological characteristics of lettuce variety NUN 07839 LTL listed in Tables 1 and 2 as determined at the 5% significance level for numerical characteristics or identical for non-numerical characteristics when grown under the same environmental conditions and/or comprising one or more (or all; or all except one, two or three) when grown under the same environmental conditions. The morphological and/or physiological characteristics may vary somewhat with variation in the environment (e.g., temperature, light intensity, day length, humidity, soil, fertilizer use), which is why a comparison under the same environmental conditions is preferred. Colors can best be measured against the Royal Horticultural Society (RHS) Chart. Also, at-harvest and/or post-harvest characteristics of heads or leaves can be compared, such as cold storage holding quality, post-harvest leaf crispness and leaf browning or pinking after cutting can be measured using known methods.

In yet another aspect, the disclosure provides for a method of producing a new lettuce plant. The method comprises crossing lettuce variety NUN 07839 LTL, or a plant of comprising all but 1, 2, or 3 of the morphological and physiological characteristics of said lettuce variety (as listed in Tables 1 and 2), or a progeny plant thereof, either as male or as female parent, with a second lettuce plant (or a wild relative of lettuce) one or more times, and/or selfing a lettuce plant of variety NUN 07839 LTL, or a progeny plant thereof, one or more times, and selecting progeny from said crossing and/or selfing. The second lettuce plant may, for example, be a line or variety of the species *Lactuca sativa*, or other *Lactuca* species.

The disclosure provides for methods of producing plants which retain all the morphological and physiological characteristics of a plant described herein. The disclosure also provides for methods of producing a plant comprising all but 1, 2, or 3 or more of the morphological and physiological characteristics of lettuce variety NUN 07839 LTL (e.g., as listed in Tables 1 and 2), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to lettuce variety NUN 07839 LTL if its DNA fingerprint is at least 80%, 90%, 95% or 98% identical to the fingerprint of lettuce variety NUN 07839 LTL. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.95 or 0.96 or more (see, e.g., "Guidelines for the Handling of a Dispute on Essential Derivation in Lettuce" at worldseed.org/wp-content/uploads/2015/10/Guidelines EDV_Lettuce_2004.pdf). the disclosure also provides a plant and a variety obtained or selected by applying these methods on lettuce variety NUN 07839 LTL. Such a plant may be produced by crossing and/or selfing, or alternatively, a plant may simply be identified and selected amongst plants of said variety, or progeny of said variety, e.g., by identifying a variant within lettuce variety NUN 07839 LTL or progeny of said variety (e.g., produced by selfing) which variant differs from lettuce variety NUN 07839 LTL in one, two or three of the morphological and/or physiological characteristics (e.g., characteristics listed in Tables 1 and 2). In one aspect, the disclosure provides a plant of lettuce variety NUN 07839 LTL having a Jaccard's Similarity index with said variety of at least 0.95, 0.96, 0.97, 0.98 or even at least 0.99.

In some aspects, the disclosure provides a lettuce plant comprising genomic DNA having at least 95%, 96%, 97%, 98%, or 99% sequence identity compared to the genomic DNA sequence of a plant of lettuce variety NUN 07839 LTL as deposited under Accession Number NCIMB 42969. In some aspects, the lettuce plant further comprises all or all but one, two, or three of the physiological and morphological characteristics of lettuce variety NUN 07839 LTL (e.g., as listed in Tables 1 and 2). In other aspects, the lettuce plant comprises the distinguishing characteristics of lettuce variety NUN 07839 LTL.

For the purpose of this disclosure, the "sequence identity" or nucleotide sequences, expressed as a percentage, refers to the number of positions in the two optimally aligned sequences which have identical residues (×100) divided by the number of positions compared. A gap, i.e., a position in the pairwise length where a residue is present in one sequence but not in the other, is regarded as a position with non-identical residues. A pairwise global sequence alignment of two nucleotide sequences is found by aligning the two consequences over the entire length according to the Needleman and Wunsch global alignment algorithm described in Needleman and Wunsch, 1970, J. Mol. Bio. 48(3):443-53. A full implementation of the Needleman-Wunsch global alignment algorithm is found in the needle program in The European Molecular Biology Open Software (see, EMBOSS, Rice, et. al., Trends in Genetics, June 2000, 16(6):276-77).

The disclosure also provides methods for determining the identity of parental lines of the plant described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of lettuce variety NUN 07839 LTL is a progeny of said variety, because the seed coat of the seed is a maternal tissue genetically identical to lettuce variety NUN 07839 LTL. Since lettuce variety NUN 07839 LTL is an inbred variety, with a very high degree of homozygosity, any F1 progeny will inherit the same, predictable, set of chromosomes from its parent. Thus, the skilled person will also be able to identify maternal tissues of a seed grown on an F1 progeny of lettuce variety NUN 07839 LTL, using the methods described in US2015/0126380. In another particular aspect, the skilled person can determine the identity of the female parental line of lettuce variety NUN 07839 LTL by analyzing the seed coat of a seed of that variety. In another aspect, the skilled person can determine whether a seed is grown on lettuce variety NUN 07839 LTL.

By crossing and/or selfing also (one or more), single traits may be introduced into, or modified in, lettuce variety NUN 07839 LTL (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into lettuce variety NUN 07839 LTL by breeding with said variety.

Any pest or disease resistance genes may be introduced into lettuce variety NUN 07839 LTL, progeny of said variety, or into a plant comprising all but 1, 2, or 3 or more of the morphological and physiological characteristics of lettuce variety NUN 07839 LTL (e.g., as listed in Tables 1 and 2). Resistance to one or more of the following diseases or pests may be introduced into the plant described herein: *Rhizomonas suberifaciens* (Corky root rot), *Bremia lactutae* (Downy mildew), *Erysiphe cichoracearum* f. sp. *lactutae* (Powdery mildew), *Sclerotinia minor* and *Sclerotinia sclerotiorum* (Lettuce Drop), *Pseudomonas* spp. (Bacterial Soft Rot), *Botrytis cinerea* (Grey Mold), *Verticillium* dahlia (*Verticillium* Wilt), *Xanthomonas* spp. (Bacterial Leaf Spot), *Microdochium panattonianum* (Anthracnose), *Fusarium oxysporum* f. sp. *lactutae*, *Rhizoctonia solani* (Bottom Rot), Cabbage Loopers, Lettuce Root Aphid, *Myzus persicae* (Green Peach Aphid), *Liriomyza langei* (Pea Leafminer), *Liriomyza trifolii* (Serpentine Leafminer), *Liriomyza sativae* (Vegetable Leafminer), Foxglove Aphid, Potato Aphid, Beet Armyworm, *Bemisia argentifolii* (Silver Whitefly), and/or Aster Yellows. Other resistance genes, against pathogenic viruses (e.g., Mirafiori Lettuce Big Vein Virus (LMBVV), Lettuce Infectious Yellows Virus (LIYV), Lettuce Mosaic Virus (LMV), Lettuce Necrotic Stunt Virus (LNSV), Cucumber Mosaic Virus (CMV), Tomato Bushy Stunt Virus (Dieback), Tomato Spotted Wilt Virus (TSWV), Turnip Mosaic Virus, Beet Western Yellows Virus (BWYV), Alfalfa mosaic virus (AMV)), fungi, bacteria, nematodes, insects or other pests may also be introduced. In one aspect, resistance against *Nasonovia ribisnigri* biotype Nr:0 and/or Nr:1 maybe introduced into the plant disclosed herein. Also, any resistances to physiological stresses may be introduced into the plant described herein, or progeny thereof or into a plant comprising all but 1, 2, or 3 or more of the morphological and physiological characteristics of said plant (e.g., as listed in Tables 1 and 2). Resistance against one or more of the following may be introduced into the plant described herein: Tip burn, Heat, Drought, Cold, Salt and/or Brown rob (Rib Discoloration/Rib Blight).

Thus, the disclosure also provides a method for developing a lettuce plant in a breeding program, using a lettuce plant described herein, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing lettuce variety NUN 07839 LTL or progeny of said variety, or a plant comprising all but 1, 2, or 3 or more of the morphological and physiological characteristics of lettuce variety NUN 07839 LTL (e.g., as listed in Tables 1 and 2) with a different lettuce plant, and wherein one or more offspring of the crossing are subject to one or more plant breeding techniques: recurrent selection, backcrossing, pedigree breeding, mass selection, mutation breeding and genetic marker enhanced selection (see, e.g., Brotman et al., Theor Appl Genet (2002) 104:1055-1063). For breeding methods in general, see, e.g., Principles of Plant Genetics and Breeding, 2007, George Acquaah, Blackwell Publishing, ISBN-13: 978-1-4051-3646-4.

The disclosure also provides a lettuce plant comprising at least a set of first set of the chromosomes of lettuce variety NUN 07839 LTL, a sample of seed of said variety has been deposited under Accession Number NCIMB 42969; optionally further comprising a single locus conversion or mutation, wherein said plant has essentially all of the morphological and physiological characteristics of the plant comprising at least a first set of the chromosomes of said variety. In another aspect, the single locus conversion or mutation confers a trait, wherein the trait is yield, nutritional value, taste, color, crunchiness, male sterility, herbicide tolerance, insect resistance, pest resistance, disease resistance, environmental stress tolerance, modified carbohydrate metabolism, or modified protein metabolism.

In one aspect, a plant of lettuce variety NUN 07839 LTL may also be mutated (by e.g., irradiation, chemical mutagenesis, heat treatment, etc.) and mutated seeds or plants may be selected in order to change one or more characteristics of said variety. Methods such as TILLING may be applied to lettuce populations in order to identify mutants. Similarly, lettuce variety NUN 07839 LTL may be transformed and regenerated, whereby one or more chimeric genes are introduced into the variety or into a plant comprising all but one, two, or three of the physiological and morphological characteristics (e.g., as listed in Tables 1 and 2). Transformation can be carried out using standard methods, such as *Agrobacterium tumefaciens* mediated transformation or biolistic, followed by selection of the transformed cells and regeneration into plants. A desired trait (e.g., gene(s) conferring pest or disease resistance, herbicide, fungicide or insecticide tolerance, etc.) can be introduced into lettuce variety NUN 07839 LTL, or progeny of said variety, by transforming said variety or progeny of said variety with a transgene that confers the desired trait, wherein the transformed plant retains all or all but one, two or three of the phenotypic and/or morphological and/or physiological characteristics of lettuce variety NUN 07839 LTL or the progeny of said variety and contains the desired trait, wherein the desired trait is yield, nutritional value, taste, color, crunchiness, male sterility, herbicide tolerance, insect resistance, pest resistance, disease resistance, environmental stress tolerance, modified carbohydrate metabolism, or modified protein metabolism.

The disclosure a method of producing a plant of lettuce variety NUN 07839 LTL having a desired trait, comprising mutating a plant or plant part of variety NUN 07839 LTL and selecting a plant the desired trait, wherein the mutated plant retains all or all but one of the physiological and morphological characteristics of said variety, optionally as described Tables 1 and 2, and contains the desired trait, and wherein a representative sample of seed of variety NUN 07839 LTL has been deposited under Accession Number NCIMB 42969. In a further aspect, the desired trait is yield, nutritional value, taste, color, crunchiness, male sterility, herbicide tolerance, insect resistance, pest resistance, disease resistance, environmental stress tolerance, modified carbohydrate metabolism, or modified protein metabolism.

In another aspect, the disclosure provides a method for inducing mutation in lettuce variety NUN 07839 LTL comprising:
a. exposing the seed, plant, plant part, or cell of lettuce variety NUN 07839 LTL to a mutagenic compound or to radiation, wherein a representative sample of seed of said variety has been deposited under Accession Number NCIMB 42969;
b. selecting the seed, plant, or plant part or cell of lettuce variety NUN 07839 LTL having a mutation; and
c. optionally growing and/or multiplying the seed, plant, plant part, or cell of lettuce variety NUN 07839 LTL having the mutation.

The disclosure also provides a plant having one, two, or three physiological and/or morphological characteristics which are different from those of lettuce variety NUN 07839 LTL, and which otherwise has all of the physiological and morphological characteristics of said variety, wherein a representative sample of seed of said variety has been deposited under Accession Number NCIMB 42969. In particular, variants which differ from lettuce variety NUN 07839 LTL in none, one, two, or three of the characteristics mentioned in Tables 1 and 2 are encompassed.

A part of lettuce variety NUN 07839 LTL (or of progeny of said variety or of a plant having all physiological and/or morphological characteristics but one, two or three which are different from those of said variety) encompasses any cells, tissues, organs obtainable from the seedlings or plants, such as but not limited to: a lettuce head or a part thereof, a leaf or a part thereof, a cutting, hypocotyl, cotyledon, seed coat, pollen and the like. Such parts can be stored and/or processed further.

The disclosure further provides for food or feed products comprising a part of lettuce variety NUN 07839 LTL or a part of progeny of lettuce variety NUN 07839 LTL, or a part of a plant having all but one, two, or three of the physiological and morphological characteristics of lettuce variety NUN 07839 LTL, comprising one or more of such parts, optionally processed (e.g., canned, chopped, cooked, roasted, in a sauce, in a sandwich, pasted, pureed or concentrated, juiced, frozen, dried, pickled, or powdered).

In one aspect, the disclosure provides for a haploid plant and/or a doubled haploid plant of variety NUN 07839 LTL, or a plant having all but one, two or three physiological and/or morphological characteristics of lettuce variety NUN 07839 LTL, or progeny of said variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for producing double haloid cells of lettuce variety NUN 07839 LTL, comprising making double haploid cells from haploids cells from the plant or plant part of lettuce variety NUN 07839 LTL with a chromosome doubling agent, such as colchicine treatment (see, e.g., Nikolova and Niemirowicz-Szczytt (1996) Acta Soc Bot Pol 65:311-317).

In another aspect, the disclosure provides for haploid plants and/or doubled haploid plants derived from lettuce variety NUN 07839 LTL that, when combined, make a set of parents of lettuce variety NUN 07839 LTL. The haploid plant and/or the doubled haploid plant of variety NUN 07839 LTL can be used in a method for generating parental lines of lettuce variety NUN 07839 LTL.

The disclosure also relates to a method of producing a combination of parental lines of a plant of variety NUN 07839 LTL, comprising making double haploid cells from haploid cells form said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of variety NUN 07839 LTL, when these parental lines are crossed. In still another aspect, the disclosure relates to a combination of a parental lines from which a seed or plant having all physiological and/or morphological characteristics of lettuce variety NUN 07839 LTL (when the characteristics are determined at the 5% significance level for plants grown under the same environmental conditions).

The disclosure also provides a combination of parental lines, which when crossed, produce a seed or plant having all of the physiological and/or morphological characteristics of lettuce variety NUN 07839 LTL, but one, two, or three which are different (when grown under the same environmental conditions).

Using methods known in the art such as "reverse synthesis of breeding lines" or "reverse breeding", it is possible to produce parental lines for a hybrid plant such as lettuce variety NUN 07839 LTL. A skilled person can take any individual heterozygous plant (called a "phenotypically superior plant" in Example 2 of US2015/0245570 hereby incorporated by reference in its entirety; lettuce variety NUN 07839 LTL is such plant) and generate a combination of parental lines (reverse breeding parental lines) that, when crossed, produce the variety NUN 07839 LTL. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., lettuce variety NUN 07839 LTL), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of lettuce variety NUN 07839 LTL, which when crossed reconstitute the genome of lettuce variety NUN 07839 LTL, comprising:
 a. defining a set genetic a) markers that are present a heterozygous form (H) in a partially heterozygous starting organism;
 b. producing at least one further generation from the starting organism by self-pollination (e.g., F2 or F3 generation);
 c. selecting at least one pair of progeny organisms in which at least one genetic marker from the set is present in a complementary homozygous forms (B vs. A, or A vs. B); and optionally repeating steps b) and c) until at least one pair of progeny organisms that have complementary alleles for at least a subset of the genetic markers has been selected as parental lines for a hybrid.

In another aspect, the disclosure provides a method of introducing a single locus conversion or single trait conversion or a desired trait into lettuce variety NUN 07839 LTL, comprising:
 a. obtaining a combination of parental lines of lettuce variety NUN 07839 LTL, optionally through reverse synthesis of breeding lines;
 b. introducing a single locus conversion in at least one of the parents of step a); and
 c. crossing the converted parent with the other parent of step a) to obtain seed of lettuce variety NUN 07839 LTL.

In another aspect, a combination of a male and a female parental line of lettuce variety NUN 07839 LTL can be generated by methods described herein, for example, through reverse synthesis of breeding lines.

In another aspect, the disclosure provides a method of introducing a single locus conversion or single trait conversion or a desired trait into lettuce variety NUN 07839 LTL, comprising introducing a single locus conversion in at least one of the parents of lettuce variety NUN 07839 LTL, and crossing the converted parent with the other parent of lettuce variety NUN 07839 LTL, to obtain seed of said variety.

In another aspect, introducing a single locus conversion in at least one of the parent plants comprises:
 a. obtaining a cell or tissue culture of cells of the parental line of lettuce variety NUN 07839 LTL;
 b. genetically transforming or mutating said cells;
 c. growing the cells into a plant; and
 d. optionally selecting a plant that contains the desired single locus conversion, single trait conversion, or the desired trait.

In another aspect, the step of introducing a single locus conversion in at least one of the parent plants comprises:
 a. crossing the parental line of lettuce variety NUN 07839 LTL, with a second lettuce plant comprising the single locus conversion, the single trait conversion, or the desired trait;
 b. selecting F1 progeny plants that contain the single locus conversion, the single trait conversion, or the desired trait.
 c. crossing said selected progeny plants of step b) with the parental line of step a) to produce a backcross progeny plant;

d. selecting backcross progeny plants comprising the single locus conversion, the single trait conversion or the desired trait and otherwise all or all but one, two, or three of the physiological and morphological characteristics of the parental line of step a) to produce selected backcross progeny plants; and e. optionally repeating steps c) and d) one or more times in succession to produce selected second, third, or fourth, or higher backcross progeny plants comprising the single locus conversion, the single trait conversion, or the desired trait and otherwise all or all but one, two, or three of the physiological and morphological characteristics of the parental line of step a) to produce selected backcross progeny plants, when grown in the same environmental conditions.

The disclosure further relates to plants obtained by this method.

In any of the above methods, wherein the single locus conversion concerns a trait, the trait may be yield or pest resistance, or disease resistance. In one aspect, the trait is disease resistance and the resistance is conferred to *Rhizomonas suberifaciens* (Corky root rot), *Bremia lactucae* (Downy mildew), *Erysiphe cichoracearum* f. sp. *lactutae* (Powdery mildew), *Sclerotinia minor* and *Sclerotinia sclerotiorum* (Lettuce Drop), *Pseudomonas* spp. (Bacterial Soft Rot), *Botrytis cinerea* (Grey Mold), *Verticillium* dahlia (*Verticillium* Wilt), *Xanthomonas* spp. (Bacterial Leaf Spot), *Microdochium panattonianum* (Anthracnose), *Fusarium oxysporum* f. sp. *lactutae, Rhizoctonia solani* (Bottom Rot), Cabbage Loopers, Lettuce Root Aphid, *Myzus persicae* (Green Peach Aphid), *Liriomyza langei* (Pea Leafminer), *Liriomyza trifolii* (Serpentine Leafminer), *Liriomyza sativae* (Vegetable Leafminer), Foxglove Aphid, Potato Aphid, Beet Armyworm, *Bemisia argentifolii* (Silver Whitefly), and/or Aster Yellows. Other resistance genes, against pathogenic viruses (e.g., Mirafiori Lettuce Big Vein Virus (LMBVV), Lettuce Infectious Yellows Virus (LIYV), Lettuce Mosaic Virus (LMV), Lettuce Necrotic Stunt Virus (LNSV), Cucumber Mosaic Virus (CMV), Tomato Bushy Stunt Virus (Dieback), Tomato Spotted Wilt Virus (TSWV), Turnip Mosaic Virus, Beet Western Yellows Virus (BWYV), Alfalfa mosaic virus (AMV)), fungi, bacteria, nematodes, insects or other pests may also be introduced. In one aspect, resistance against *Nasonovia ribisnigri* biotype Nr:0 and/or Nr:1 maybe introduced into the plant disclosed herein. Also, any resistances to physiological stresses may be introduced into the plant described herein, or progeny thereof or into a plant comprising all but 1, 2, or 3 or more of the morphological and physiological characteristics of said plant (e.g., as listed in Tables 1 and 2). Resistance against one or more of the following may be introduced into the plant described herein: Tip burn, Heat, Drought, Cold, Salt and/or Brown rob (Rib Discoloration/Rib Blight).

Also provided is a plant part obtainable from variety NUN 07839 LTL (or from progeny of said variety or from a plant having all but one, two or three physiological and/or morphological characteristics which are different from those of lettuce variety NUN 07839 LTL) or from a vegetatively propagated plant of variety NUN 07839 LTL (or from its progeny or from a plant having all but one, two or three physiological and/or morphological characteristics which are different from those of lettuce variety NUN 07839 LTL), wherein the plant part is a leaf, a harvested leaf, a part of a leaf, a head, a harvested head, a part of a head, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on lettuce variety NUN 07839 LTL, or a hypocotyl, a cotyledon, a pistil, an anther, or a flower or a part thereof.

In another aspect, the disclosure provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

The disclosure also provides for a food or feed product comprising or consisting of a plant part described herein. Preferably, the plant part is a lettuce leaf, or a lettuce head or another plant part described herein. The food or feed product may be fresh or processed, e.g., dried, grinded, powdered, pickled, chopped, cooked, roasted, in sauce, in a sandwich, pasted, pureed or concentrated, juiced, pickled, canned, steamed, boiled, fried, blanched, and/or frozen, etc.

All documents (e.g., patent publications) are herein incorporated by reference in their entirety, including the following cited references:

US Department of Agriculture, Agricultural Marketing Service, "Objective Description of Variety—Lettuce (*Lactuca sativa* L.)", world wide web at ams.usda.gov/services/plant-variety-protection/pvpo-c-forms, under lettuce.

UPOV, "Guidelines for the Conduct of Tests for Distinctness, Uniformity and Stability", TG/13/11 (Geneva 2006, last updated 2017 Apr. 5), world-wide web at upov.int under edocs/tgdocs/en/tg013.pdf Acquaah, G., "Principles of Plant Genetics and Breeding", Blackwell Publishing, 2007, ISBN-13: 978-1-4051-3646-4.

Brotman, Y., et. al., "Resistance Gene Homologues in Melon are Linked to Genetic Loci Conferring Disease and Pest Resistance", Theor Appl Genet, 2002, vol. 104, pp. 1055-1063, DOI 10.1007/s00122-001-0808-x Gonai, T., et al., "Abscisic Acid in the Thermoinhibition of Lettuce Seed Germination and Enhancement of its Catabolism by Gibberellin", Journal of Experimental Botany, 2004, vol. 55(394), pp. 111-118.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Teng, W., et al., "Rapid Regeneration of Lettuce from Suspension Culture", HortScience, 1992, vol. 27(9), pp. 1030-1032.

Teng, W., et al., "Regenerating Lettuce from Suspension Culture in a 2-Liter Bioreactor", HortScience, 1993, vol. 28(6), pp. 669-671.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

Zhang, X., et al., "Genotypic Effects on Tissue Culture Response of Lettuce Cotyledons", Journal of Genetics and Breeding, 1992, vol. 46, pp. 287-290.

US 2008/0222949
EP 1 197 137 A1
US2015/0126380
http://anrcatalog.ucanr.edu/pdf/7215.pdf
http://anrcatalog.ucanr.edu/pdf/7216.pdf
https://www.ams.usda.gov/sites/default/files/media/01-Lettuce %20ST-470-01%202015.pdf
https://www.upov.int/edocs/tgdocs/en/tg013.pdf
http://www.worldseed.org/wp-content/uploads/2015/10/Guidelines_EDV_Lettuce_2004.pdf Development of Lettuce Variety NUN 07839 LTL The inbred variety NUN 07839 LTL was developed from an initial cross between lettuce lines. The female and male parents were crossed to produce seeds. After the cross, progeny was self-pollinated or backcrossed, followed by pedigree selection and line selection. Lettuce variety NUN 07839 LTL can be propagated by seeds or vegetatively, or by regeneration of a tissue culture. The seeds of lettuce variety NUN 07839 LTL can be grown to produce inbred plants and parts thereof (e.g., lettuce heads and leaves).

The Applicant concluded that lettuce variety NUN 07839 LTL is uniform and stable. This has been established through evaluation of horticultural characteristics. Several seed production events resulted in no observable deviation in genetic stability.

Deposit Information

A total of 2500 seeds of variety NUN 07839 LTL were deposited according to the Budapest Treaty by Nunhems B.V. on Feb. 13, 2018 at the NCIMB Ltd., Ferguson Building, Craibstone Estate, Bucksburn, Aberdeen AB21 9YA, United Kingdom (NCIMB). The deposit has been assigned NCIMB 42969. A deposit of lettuce variety NUN 07839 LTL is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq.).

Characteristics of Lettuce Variety NUN 07839 LTL

The most similar variety to NUN 07839 LTL is referred to as NUN 9044 LT, a variety from Nunhems B.V. with the commercial name Redglace.

In Tables 1 and 2, a comparison between lettuce variety NUN 07839 LTL and Reference Variety NUN 9044 LT is shown based on a trial in the USA. Trial location: Acampo, USA; Transplanting date: Oct. 24, 2018; Harvesting date: Feb. 25, 2019. In Table 3, the distinguishing characteristics between lettuce variety NUN 07839 LTL and the Reference Variety are shown.

One replication of 30 plants of each variety, from which at least 15 plants or plant parts were randomly selected and were used to measure characteristics. For numerical characteristics, averages were calculated. For non-numerical characteristics, the type/degree was determined.

In one aspect, the disclosure provides a plant having all of the physiological and morphological characteristics of lettuce variety NUN 07839 LTL as presented in Tables 1 and 2.

TABLE 1

Objective Description of Lettuce Variety NUN 07839 LTL and the Reference Variety NUN 9044 LT (USDA descriptors); where the quantitative values are mentioned these are statistically significantly different between lettuce variety NUN 07839 LTL and the Reference Variety using an ANOVA Tukey test.

| Characteristics | NUN 07839 LTL | NUN 9044 LT (Redglace) |
|---|---|---|
| Plant type | | |
| 1 = Cutting/Leaf; 02 = Butterhead; 03 = Bibb; 04 = Cos or Romaine; 05 = Great Lakes Group; 06 = Vanguard Group; 07 = Salinas Group; 08 = Eastern (Ithaca) Group; 09 = Stem; 10 = Latin; 11 = Other (Specify) | Cutting/leaf | Cutting/leaf |
| Cotyledon to fourth leaf stage | | |
| Length at $4^{th}$ leaf (mm): | 42.41 | 34.6 |
| Width at $4^{th}$ leaf (mm): | 22.4 | 25.8 |
| Length/width index of $4^{th}$ leaf (mm): | 18.9 | 13.4 |
| Apical margin: 1 = Entire; 2 = Crenate/Gnawed; 3 = Finely Dentate; 4 = Moderately Dentate; 5 = Coarsely Dentate; 6 = Incised; 7 = Lobed; 8 = Other | Entire | Coarsely dentate |
| Basal margin: | Coarsely dentate | Moderately dentate |
| Undulation: 1 = Flat; 2 = Slight; 3 = Medium; 4 = Marked | Slight | Medium |

TABLE 1-continued

Objective Description of Lettuce Variety NUN 07839 LTL and the Reference Variety NUN 9044 LT (USDA descriptors); where the quantitative values are mentioned these are statistically significantly different between lettuce variety NUN 07839 LTL and the Reference Variety using an ANOVA Tukey test.

| Characteristics | NUN 07839 LTL | NUN 9044 LT (Redglace) |
|---|---|---|
| Anthocyanin: | | |
| Distribution: 1 = Absent; 2 = Margin only; 3 = Spotted; 4 = Throughout; 5 = Other (specify) | Throughout | Throughout |
| Concentration: 1 = Light; 2 = Moderate; 3 = Intense | Intense | Intense |
| Cupping: 1 = Uncupped; 2 = Slight; 3 = Markedly | Uncupped | Uncupped |
| Reflexing: 1 = None; 2 = Apical margin; 3 = Lateral margins | None | None |
| Mature leaves (harvest-mature outer leaves) Margin: | | |
| Incision depth (deepest penetration of the margin): 1 = Absent/Shallow (Dark Green Boston); 2 = Moderate (Vanguard); 3 = Deep (Great Lakes 659) | Deep | Moderate |
| Incision density (on margin on apical part): 3 = Sparse; 5 = Medium; 7 = Dense; 9 = Very Dense | Medium | Very dense |
| Indentation (finest divisions of the margin): 1 = Entire; 2 = Shallowly Dentate (Great Lake 65); 3 = Deeply Dentate (Great Lake 659); 4 = Crenate (Vanguard); 5 = Other (Specify) | Shallowly dentate | Crenate |
| Undulations of the apical margin: 1 = Absent/Slight (Dark Green Boston); 2 = Moderate (Vanguard); 3 = Strong (Great Lakes 659) | Moderate | Strong |
| Mature leaf color: | RHS N186A | RHS 187A |
| Anthocyanin: | | |
| Concentration: 1 = Light (Iceberg); 2 = Moderate (Prize Head); 3 = Intense (Ruby) | Intense | Intense |
| Size: 1 = Small; 2 = Medium; 3 = Large | Medium | Medium |
| Glossiness: 1 = Dull (Vanguard); 2 = Moderate (Salinas); 3 = Glossy (Great Lakes) | Moderate | Moderate |
| Blistering: 1 = Absent/Slight (Salinas); 2 = Moderate (Vanguard); 3 = Strong (Prize Head) | Moderate | Absent |
| Leaf thickness: 1 = Thin; 2 = Intermediate; 3 = Thick | Intermediate | Intermediate |
| Trichomes: 1 = Absent (Smooth); 2 = Present (Spiny) | Absent | Absent |
| Plant | | |
| Spread of frame leaves (cm): | 36.6 | 25.74 |
| Head shape: 1 = Flattened; 2 = Slightly Flattened; 3 = Spherical; 4 = Elongate, 5 = Non-heading; 6 = Other (Specify) | Non-heading | Non-heading |
| Head size class: 1 = Small; 2 = Medium; 3 = Large | Medium | Small |
| Head Weight (grams): | 319.4 | 82.3 |
| Head firmness: 1 = Loose; 2 = Moderate; 3 = Firm; 4 = Very Firm | Loose | Loose |
| Butt | | |
| Shape: 1 = Slightly concave; 2 = Flat; 3 = Rounded | Rounded | Rounded |
| Midrib: Flattened (Salinas); 2 = Moderately raised; 3 = Prominently raised (Great Lakes 659) | Moderately raised | Moderately raised |

TABLE 1-continued

Objective Description of Lettuce Variety NUN 07839 LTL and the Reference Variety NUN 9044 LT (USDA descriptors); where the quantitative values are mentioned these are statistically significantly different between lettuce variety NUN 07839 LTL and the Reference Variety using an ANOVA Tukey test.

| Characteristics | NUN 07839 LTL | NUN 9044 LT (Redglace) |
|---|---|---|
| Core | | |
| Diameter at base of head (mm): | 21 | 9.9 |
| Ratio of head spread/core diameter: | 1.74 | 2.6 |
| Average core height from base of head to apex (mm): | 20.1 | 11.01 |
| Range of core height from base of head to apex (mm): | 16.50-24.65 | 8.63-17.05 |
| Maturity: | | |
| Winter | 124 days | |
| Adaptation | | |
| Primary regions of adaptation: 0 = Not Tested; 1 = Not Adapted; 2 = Adapted | | |
| Southwest (CA and/or AZ desert) | | |
| West Coast | Adapted | Adapted |
| Northeast | Adapted | Adapted |
| North Central | Not tested | Not tested |
| Southeast | Not tested | Not tested |
| Other | Not tested | Not tested |
| Season: | | |
| Spring | Adapted (West Coast) | Adapted (West Coast) |
| Summer | Adapted (West Coast) | Adapted (West Coast) |
| Fall | Adapted (West Coast) | Adapted (West Coast) |
| Winter | Adapted (Southwest/West Coast) | Adapted (Southwest/West Coast) |

TABLE 2

Objective Description of Lettuce Variety NUN 07839 LTL and the Reference Variety NUN 9044 LT (Non-USDA descriptors); where the quantitative values are mentioned these are statistically significantly different between lettuce variety NUN 07839 LTL and the Reference Variety using an ANOVA Tukey test.

| Characteristics | NUN 07839 LTL | NUN 9044 LT (Redglace) |
|---|---|---|
| Mature leaves: | | |
| Mature leaf length (mm) | 203.3 | 134.7 |
| Mature leaf width (mm) | 141.1 | 130.0 |
| Plant: | | |
| Plant height (cm) | 16.88 | 15.1 |

TABLE 3

Distinguishing Characteristics between Lettuce Variety NUN 07839 LTL and the Reference Variety NUN 9044 LT

| Characteristics | NUN 07839 LTL | NUN 9044 LT (Redglace) |
|---|---|---|
| Coytledon to fourth leaf stage: | | |
| Length at 4$^{th}$ leaf (mm): | 42.41 | 34.6 |
| Width at 4$^{th}$ leaf (mm): | 22.4 | 25.8 |
| Length/width index of 4$^{th}$ leaf (mm): | 18.9 | 13.4 |
| Apical margin: | Entire | Coarsely dentate |
| Basal margin: | Coarsely dentate | Moderately dentate |
| Undulation: | Slight | Medium |
| Mature leaves: | | |
| Mature leaf length (mm) | 203.3 | 134.7 |
| Mature leaf width (mm) | 141.1 | 130.0 |
| Incision depth (deepest penetration of the margin): | Deep | Moderate |
| Incision density (on margin on apical part): | Medium | Very dense |
| Indentation (finest divisions of the margin): | Shallowly dentate | Crenate |
| Undulations of the apical margin: | Moderate | Strong |
| Mature leaf color: | RHS N186A | RHS 187A |
| Blistering: | Moderate | Absent |
| Plant: | | |
| Plant height (cm) | 16.88 | 15.1 |
| Core: | | |
| Average core height from base of head to apex (mm): | 20.1 | 11.01 |
| Diameter at base of head (mm): | 21 | 9.9 |
| Ratio of head spread/core diameter: | 1.74 | 2.6 |

The invention claimed is:

1. A plant, plant part, or seed of lettuce variety NUN 07839 LTL, wherein a representative sample of seed of said variety has been deposited under Accession Number NCIMB 42969.

2. The plant part of claim 1, wherein the plant part is a head, a leaf, pollen, an ovule, a fruit, a scion, a rootstock, a cutting, a flower, or a cell.

3. A seed from which the plant of claim 1 can be grown.

4. A seed grown on the plant of claim 1.

5. A lettuce plant having all the physiological and morphological characteristics of the plant of claim 1.

6. A seed that produces the plant of claim 5.

7. A tissue or cell culture of regenerable cells of the plant of claim 1.

8. The tissue or cell culture according to claim 7, comprising cells or protoplasts derived from a plant part suitable for vegetative reproduction, wherein the plant part is an embryo, a meristem, a cotyledon, a hypocotyl, pollen, a leaf, an anther, a root, a root tip, a pistil, a petiole, a flower, a fruit, a seed, a stem, or a stalk.

9. A lettuce plant regenerated from the tissue or cell culture of claim 7, wherein the plant has all of the physiological and morphological characteristics of the plant of lettuce variety NUN 07839 LTL, wherein a representative sample of seed of said lettuce variety has been deposited under Accession Number NCIMB 42969.

10. A method of producing of the plant of claim 1, or a part thereof, said method comprising vegetative propagation of the plant of lettuce variety NUN 07839 LTL, wherein a representative sample of seed of said lettuce variety has been deposited under Accession Number NCIMB 42969.

11. The method of claim 10, wherein said vegetative propagation comprises regenerating a whole plant from a part of lettuce variety NUN 07839 LTL, wherein a representative sample of seed of said lettuce variety has been deposited under Accession Number NCIMB 42969.

12. The method of claim 10, wherein said part is a cutting, a cell culture, or a tissue culture.

13. A vegetative propagated plant of claim 1, or a part thereof, wherein the plant has all of the physiological and morphological characteristics of lettuce variety NUN 07839 LTL.

14. A method of producing a lettuce plant, comprising crossing the plant of claim 1 with a second lettuce plant at least once, and selecting a progeny lettuce plant from said crossing and allowing the progeny lettuce plant to form seed.

15. A first generation progeny of the lettuce plant of claim 1 obtained by crossing the plant of lettuce variety NUN 07839 LTL with itself or another lettuce plant.

16. A food or feed product comprising the plant part of claim 2.

17. A plant of lettuce variety NUN 07839 LTL further comprising a transgene conferring a desired trait and otherwise having all of the morphological and physiological characteristics of the plant of claim 1, when grown under the same environmental conditions, wherein a representative sample of seed of said lettuce variety has been deposited under Accession Number NCIMB 42969, wherein the desired trait is yield, storage properties, color, male sterility, herbicide tolerance, insect resistance, pest resistance, disease resistance, environmental stress tolerance, modified carbohydrate metabolism, or modified protein metabolism.

18. A method of producing a plant of lettuce variety NUN 07839 LTL having a desired trait, comprising mutating a plant of lettuce variety NUN 07839 LTL and selecting a plant having the desired trait, wherein a representative sample of seed of said variety has been deposited under Accession Number NCIMB 42969.

19. The method of claim 18, wherein the desired trait is yield, storage properties, color, male sterility, herbicide tolerance, insect resistance, pest resistance, disease resistance, environmental stress tolerance, modified carbohydrate metabolism, or modified protein metabolism.

20. A container comprising the plant, plant part, or seed of claim 1.

* * * * *